United States Patent
Liang et al.

(10) Patent No.: US 9,308,173 B2
(45) Date of Patent: Apr. 12, 2016

(54) SLOW-RELEASING OPHTHALMIC COMPOSITIONS COMPRISING POVIDONE IODINE

(71) Applicant: JIANGSU DEDA PHARMACEUTICALS CO., LTD., Taizhou, Jiangsu (CN)

(72) Inventors: Bo Liang, Plainsboro, NJ (US); John J. Baldwin, Gwynedd Valley, PA (US); Yong Lu, Taixing (CN)

(73) Assignee: IVIEW THERAPEUTICS, INC., Wilmington, DE (US)

( * ) Notice: Subject to any disclaimer, the term of this patent is extended or adjusted under 35 U.S.C. 154(b) by 0 days.

(21) Appl. No.: 14/361,242

(22) PCT Filed: Nov. 28, 2012

(86) PCT No.: PCT/CN2012/085456
§ 371 (c)(1),
(2) Date: May 28, 2014

(87) PCT Pub. No.: WO2013/078998
PCT Pub. Date: Jun. 6, 2013

(65) Prior Publication Data
US 2014/0322345 A1 Oct. 30, 2014

(30) Foreign Application Priority Data
Nov. 29, 2011 (CN) .......................... 2011 1 0386554

(51) Int. Cl.
| | |
|---|---|
| A61K 9/16 | (2006.01) |
| A61K 33/18 | (2006.01) |
| A61K 9/08 | (2006.01) |
| A61K 31/79 | (2006.01) |
| A61K 31/167 | (2006.01) |
| A61K 31/245 | (2006.01) |
| A61K 45/06 | (2006.01) |
| A61K 9/00 | (2006.01) |
| A61K 47/02 | (2006.01) |
| A61K 47/10 | (2006.01) |
| A61K 47/38 | (2006.01) |

(52) U.S. Cl.
CPC ............. *A61K 9/1652* (2013.01); *A61K 9/0051* (2013.01); *A61K 9/08* (2013.01); *A61K 31/167* (2013.01); *A61K 31/245* (2013.01); *A61K 31/79* (2013.01); *A61K 33/18* (2013.01); *A61K 45/06* (2013.01); *A61K 47/02* (2013.01); *A61K 47/10* (2013.01); *A61K 47/38* (2013.01)

(58) Field of Classification Search
None
See application file for complete search history.

(56) References Cited

U.S. PATENT DOCUMENTS

| 7,300,667 | B1 | 11/2007 | Fleischer et al. | |
|---|---|---|---|---|
| 2004/0204399 | A1 | 10/2004 | Osbakken et al. | |
| 2004/0241214 | A1* | 12/2004 | Kirkwood et al. | ............ 424/445 |
| 2005/0084534 | A1* | 4/2005 | Ni et al. | ......................... 424/488 |
| 2006/0014786 | A1* | 1/2006 | Raut | ............................ 514/310 |
| 2006/0280809 | A1 | 12/2006 | Leshchiner et al. | |
| 2009/0263345 | A1 | 10/2009 | Capriotti et al. | |
| 2010/0168074 | A1 | 7/2010 | Culligan et al. | |

FOREIGN PATENT DOCUMENTS

| EP | 1870089 A1 | 12/2007 |
|---|---|---|
| EP | 2201940 A1 | 6/2010 |
| WO | 0072823 A1 | 12/2000 |
| WO | WO 2007106381 A2 * | 9/2007 |
| WO | 2011084473 A1 | 7/2011 |

OTHER PUBLICATIONS

SK Motwani, S Chopra, S Talegaonkar, K Kohli, FJ Ahmad, RK Khar. "Chitosan-sodium alginate nanoparticles as submicroscopic reservoirs for ocular delivery: Formulation, optimisation and in vitro characterisation." European Journal of Pharmaceutics and Biopharmaceutics, vol. 68, 2008, pp. 513-525.*

Wu Qin-hui et al, Review on preparation and application of Alginate microspheres as drug carrier, China Journal of Traditional Chinese Medicine and Pharmacy, 2011, vol. 26, No. 8, pp. 1791-1794, see the abstract, p. 1792, light column, Only abstract was considered as only abstract is in English.

* cited by examiner

*Primary Examiner* — Isaac Shomer
(74) *Attorney, Agent, or Firm* — Weisun Rao; Greenberg Traurig, LLP

(57) ABSTRACT

The present invention provides novel slow-releasing ophthalmic compositions containing Povidone Iodine (PVP-I) and uses thereof in the treatment of acute infections of at least one eye tissue from bacterial, mycobacterial, viral, fungal, or amoebic causes and for preventing such infections in appropriate clinical settings. Each of the ophthalmic compositions contains povidone iodine, osmotic pressure regulator, suspending agent and EDTA-Na, wherein povidone iodine exists as microsphere particles formed by PVP-I and sodium alginate.

36 Claims, No Drawings

SLOW-RELEASING OPHTHALMIC COMPOSITIONS COMPRISING POVIDONE IODINE

CROSS-REFERENCE TO RELATED APPLICATIONS

This application is a national phase application and claims benefit under 35 U.S.C. §371 of PCT/CN2012/085456, filed on Nov. 28, 2012, which in turn claims priority to Chinese patent application No. 201110386554.6, filed on Nov. 29, 2011, the contents of which are incorporated herein by reference in their entireties.

BACKGROUND OF THE INVENTION

Infectious conjunctivitis is an ophthalmic disorder characterized by inflammation of the conjunctiva secondary to invasion of a microbe. Microbes are capable of causing conjunctivitis in humans include bacteria (including Mycobacteria sp), viruses, fungi, and amoebae. Current treatments for bacterial conjunctivitis consist of antibiotic drops. Because antibiotic drops are ineffective against viral conjunctivitis, treatments for such infections can only relieve symptoms. Treatments for fungi and amoeba conjunctivitis consist of a small selection of medications which lack sufficient antibacterial or anti-viral activity and are sometimes toxic to the ocular surface.

Diagnosis of the various causative agents such as bacteria, virus, or fungus, in infectious conjunctivitis is not economically feasible because accurate diagnosis requires sophisticated laboratory culture not easily integrated into the average healthcare practice. Because accurate diagnosis is impractical, most conjunctivitis is presumed to be bacterial without culturing and is treated with antibiotics. Antibiotic treatment is suboptimal because it is ineffective against viral or fungal conjunctivitis. In summary, there is currently no ophthalmic antimicrobial drug that has broad activity against all the causes of conjunctivitis or keratitis and can be safely used in infectious conjunctivitis or keratitis that can potentially be viral or fungal in origin.

Ophthalmic topical drug delivery is one of the important methods of application, but the existence of cornea barrier, tears' dilution and lacrimal passage's drainage effect limit the treatments and bioavailability of many topical ophthalmic preparations, especially for the posterior segment disease. In order for a high concentration in the Eyeball Vitreous, repeated intraperitoneal drug administration is necessary. However, repeated administration increases not only the patient's discomfort, but also the risk of operations and complications. On the other hand, ophthalmic drugs can be absorbed in nasal and oral cavity which increases the toxic or side effects during the treatment. Therefore for local effectiveness, many researchers want to explore a new drug carrier system to maintain the drug concentration for a longer period time, to increase effectiveness and to decrease the risk of complications and to gain the treatment goal. In recent years, many researches find that lots of slow and controlled-releasing agent like liposome and microsphere can maintain drug release for a longer time, and decrease the frequency of drug administration, reduce the drug concentration peak phenomenon, reduce the dosage and the toxicity. Biodegradable microspheres, compared to other agents, have the advantages of simple preparation, better stability and lower cost etc. Among all the drug delivery systems, only the microsphere formulations and solid implants can really result in controlled release, and microspheres formulations have the additional advantage of suspendability in a medium used as eye drops reducing the discomfort in the eyes.

Microspheres are microspherical entities formed by dissolving or dispersing drugs in excipients. They are fine and uniform particles, can encapsulate drugs with poor water-solubility, and can be used to prepare drug formulations with sustained effected or for special targets. Usually those with particle size in the range of 1-250 μm are called microspheres, and those between 10-1000 nm are called nanoparticles. Commonly used particles have the size of 200 nm to 40 μm, and those used for ocular drug-delivery have the particle size no more than 10 μm, otherwise patients will feel ocular irritation. If the particles remain in the eyes after the drug-carrying microspheres drop into eyes, the microspheres will be more suitable for sustained and controlled release. As such, preparation of particle-based pharmaceutical formulations typically has a more stringent requirement for the control of the particle size. Among others, pilocarpine, β-receptor blockers, chloramphenicol, hydrocortisone, and Amikacin have been made into such formulations.

Povidone iodine (PVP-I) is a complex of polyvinylpyrrolidone and iodine. It is also called iodophor and contains 9-12% effective iodine. It is a powerful disinfectant with a broad spectrum of applications and is strongly effective against viruses, bacteria, fungi, and mold spores. It causes little irritation on skin and has low toxicity and lasting effect, and can be used safely and easily. It basically does not cause irritation on tissue and widely used for skin and mucous membrane's disinfection, e.g., for pre-surgical cleaning and disinfection of surgical site and wound. The principle of sterilization is mainly through the release of hydrated iodine which has bactericidal effect. Povidone is hydrophilic and can carry iodine to cell membrane. When the complex arrives at the cell wall, the iodine is released and then complexes with amino acids of bacterial protein to denature it and, at the same time, oxidize the active groups of the bacteria's protoplasmic protein so that the bacteria dies rapidly. Povidone iodine is a very good bactericidal agent with no antibiotic resistance. In common use, povidone iodine's concentration is between 0.1% and 10%. Current povidone iodine preparations are in the forms of gel, suppository, cream, solution, with concentration ranging from 1% to 10%. (See Chinese Pharmacopoeia 2010 Edition). Povidone iodine eye drops have been widely used for the treatment of ocular infection basically with high concentrations of 5% with toxic effects that cannot be ignored. Grimes and others treated infected eyes repeatedly with 0.02% PVP-I eye drop which has the same germicidal effects as one with concentration of 5.0% povidone iodine but without the toxic affection and irritation. (See Grimes S R et al., Mil. Med., 1992, 157:111-113.) In order to retain a povidone iodine eye drop' sterilizing effect, but also to eliminate its toxicity to eyes, clinical operation usually use PVP-I eye drops with concentration of 0.04% to disinfect eyes with no noticeable toxicity. However, at a low concentration, povidone iodine will degrade quickly and its concentration cannot be effectively maintained at the infected site due to the tear barrier effects. Therefore, in order to reduce the toxic effect on the eyes by povidone iodine at a high concentration meanwhile maintaining its pharmaceutical effect at the infected site, it is often necessary to prepare formulations with low toxicity and long-lasting effect. Among those currently controlled release formulations used for the eyes, ocular implants and microspheres formulations are more practical. In the treatment of ocular infections, application of ocular implants in the infected sites needs assistance by a physician, thereby greatly decreasing the patients' medication compliance.

As a result of strong oxidizing potential and acidity of povidone iodine, it is difficult to prepare povidone iodine microspheres from commonly used microsphere materials. Meanwhile, however, the microparticle technologies cannot be used to prepare effective system for the slow release of povidone iodine in the eyes.

SUMMARY OF THE INVENTION

The mammalian eye can be divided into two main segments: the anterior segment and the posterior segment. The anterior segment is the front third of the eye that includes the tissues in front of the vitreous humor: the cornea, iris, ciliary body, and lens. Within the anterior segment are two fluid-filled spaces: the anterior chamber and the posterior chamber. The anterior chamber is located between the posterior surface of the cornea (i.e. the corneal endothelium) and the iris. The posterior chamber is located between the iris and the front face of the vitreous. The posterior segment is the back two-thirds of the eye that includes the anterior hyaloid membrane and all tissues behind it: the vitreous humor, retina, choroid, and optic nerve. In some animals, the retina contains a reflective layer (the tapetum lucidum) which increases the amount of light each photosensitive cell perceives, allowing the animal to see better under low light conditions.

The present invention generally relates to ophthalmic compositions each comprising a pharmaceutically acceptable excipient (e.g., water) and povidone-iodine (PVP-I) in microspheres formed by PVP-I and sodium alginate, and methods for using same for the treatment or prophylaxis of a disorder of at least one eye tissue. These ophthalmic compositions have the unexpected advantage of long stability (even under light) in an acidic environment (e.g., pH 1~%) and are able to slowly release PVP-I in a controlled manner over an extended period of time in a neutral environment (e.g., pH 6.8-7.2) which is an ideal ophthalmic slow-release system.

In some embodiments, the concentration of PVP-I in the ophthalmic compositions ranges from about 0.01% to about 10% (weight/weight or weight/volume), e.g., from about 0.01% to about 5%, from about 0.1% to about 5%, from about 0.1 to 2.5%, or from about 0.4 to about 2.0%, all by weight.

In some embodiments, the PVP-I microspheres' size ranges from 10 nm to 500 μm, e.g., from 10 nm to 1,000 nm, from 1 μm to 500 μm, from 1 μm to 250 μm, from 1 μm to 100 μm, from 100 nm to 100 μm, from 200 nm to 100 μm, from 200 nm to 10 μm, from 200 nm to 1,000 nm, from 500 nm to 1,000 nm, or from 10 nm to 500 nm.

In some embodiments, the weight ratio of PVP-I and sodium alginate in the microspheres ranges from about 1:1 to about 1:5 (e.g., 1:1.2, 1:1.5, 1:1.8, 1:2, 1:2.5, 1:3, 1:3.5, 1:4, or 1:4.5).

In some embodiments, the ophthalmic composition further includes calcium chloride and PVP-I (not in the microspheres) as stabilizing agents for the microspheres. The concentration of calcium chloride in the composition can range from about 0.08% to about 0.5% (e.g., from about 0.1% to about 0.5%, from about 0.1% to about 0.3%, from about 0.1% to about 0.25%, or from 0.2% to 0.25%) by weight. High calcium concentration may potentially lead to the risk of cataract. Calcium chloride can also be used as microsphere curing agent in preparation of microspheres with the preferred concentration by 1%-5%. The concentration of PVP-I as stabilizing agent can range from about 0.1% to about 5% (e.g., from about 0.1% to about 2.5%, from about 0.1% to about 1%, from 0.2% to about 2.5%, from 0.5% to about 2.5%) by weight.

In some embodiments, the microspheres' concentration in the composition ranges from about 1% to about 25% (e.g., from about 1% to about 15%, from about 1% to about 10%, from about 5% to about 25%, from about 5% to about 10%, or from about 2.5% to about 10%) by weight.

In some embodiments, the ophthalmic composition further includes an osmotic pressure regulator, a suspending agent, a chelating agent, a preservative, a coolant, a surfactant, a wetting agent, an anti-oxidant, and a binder.

The osmotic pressure regulator can be glycerin, mannitol, or sorbitol, sodium chloride, or any combination thereof; and the osmotic pressure regulator's concentration can range from about 0.03% to about 2% (e.g., from 0.03% to 1.0%, from 0.05% to about 1.0%, from 0.1% to 1.0%, or from 0.5% to about 1.0%) by weight. The preferred choice is sodium chloride.

from about 0.01% to about 1.5%, from about 0.01% to about 1%, The suspending agent can be methylcellulose, hydroxypropyl methyl cellulose, hydroxyethyl cellulose, hydroxyl propyl cellulose, microcrystalline cellulose, sodium carboxymethyl cellulose, propylene glycol alginate, or any combination thereof; and the suspending agent's concentration can range from about 0.01% to about 2% (e.g., from about 0.05% to about 1.5%, from about 0.05% to about 1%, from about 0.1% to about 1%, from about 0.1% to about 0.5%, or from about 0.1% to about 1.5%) by weight.

Examples of suitable chelating agent include hydroxide compounds, citric acid salt, phosphate, hydrochloride, sulfite salts, EDTA, and EDTA salts (e.g., EDTA-Na), with a preferred concentration of 0.01%~0.05% by weight.

The wetting agent can be an alcohol (e.g., ethanol or propanol), propylene glycol, glycerin, polyethylene glycol 200~400, or any combination thereof; and the concentration of the wetting agent can range from about 0.1% to 10% (e.g., from about 0.1% to 5%, from about 0.1% to 2%, from about 0.1% to 1%, from about 0.2% to 5%, from about 0.2% to 2.5%, from about 0.2% to 1%, from about 0.5% to 1%, or about 0.75%) by weight.

The surfactant can be polysorbate 20, polysorbate 60, polysorbate 80, Pluronic F-68, Pluronic F-84, Pluronic P-103, cyclodextrin, tyloxapol, Tween 80, cyclodextrin, polyethylene glycol, castor oil, polyethylene glycol 40, and stearic acid, or any combination thereof; and the concentration of the surfactant can range from about 0.01% to about 2% (e.g., from about 0.01% to about 1.5%, from about 0.01% to about 1%, from about 0.01% to about 0.5%, from about 0.01% to about 0.2%, from about 0.01% to about 0.1%, or from about 0.1% to about 1%) by weight.

Examples of suitable coolant include ethanol, menthol, borneol, eucalyptus oil, dimethyl silicone oil, and mint. The preferred concentration of the coolant is between 0.01% and 0.5% of total weight of composition.

The ophthalmic composition may further comprise preservatives selected from the group of organomercury, quaternary ammonium salts, spring one or several. Quaternary ammonium salt is preferred; and preferred to be benzalkonium bromide. The preservative's concentration is preferred to be 0.01%~1% of total weight of eye drops.

The ophthalmic composition may further comprise one or more antioxidants selected from the group of aromatic amines, phenols, propionic acid diester, phosphite ester, hydrogen peroxide, among which hydrogen peroxide is preferred. The optimum concentration of antioxidant is from about 0.01% to about 0.5% by weight.

Examples of suitable binder include sodium hyaluronate, sodium alginate, proteins, acrylic resin, butadiene resin, polyurethane, and nitric acid fiber. sodium hyaluronate is preferred. The preferred concentration of the binder is 0.01%~0.1% in the total weight of the composition.

Examples of co-solvent include ethanol, glycerol, propylene glycol, polyethylene glycol. Ethanol is preferred. The preferred co-solvent concentration is 0.5%~5% in the total weight of the composition.

Examples of suitable pH adjusters can include phosphoric acid and its salts, boric acid and its salt, citric acid and its salts, acetic acid and its salts, tartaric acid and its salts, hydrochloric acid, sodium hydroxide, potassium carbonate, sodium carbonate, sodium bicarbonate, potassium bicarbonate, tromethamine and so on. Among them, hydrochloric acid and sodium hydroxide are commonly used.

In some embodiments, the ophthalmic composition further includes a topical anesthetic which relieves pain. Examples of suitable topical anesthetic include, e.g., proparacaine, lidocaine, tetracaine, and any combination thereof.

In some embodiments, the ophthalmic composition further includes a penetration enhancer which enhances the penetration of PVP-I into the eye tissue. The penetration enhancer can be a topical anesthetic at the same time.

In some embodiments, the ophthalmic composition further includes an antimicrobial preservative. Examples of the antimicrobial preservative include benzalkonium chloride, thimerosal, chlorobutanol, methyl paraben, propyl paraben, phenylethyl alcohol, EDTA, sorbic acid, Onamer M, and any combination thereof. The antimicrobial preservative can have a concentration ranging from about 0.001% to about 1.0% (e.g., from about 0.001% to about 1.0%, from about 0.01% to about 1.0%, from about 0.1% to about 1.0%, from about 0.005% to about 0.1%, from about 0.01% to about 0.1%, from about 0.01% to about 0.5%, or from about 0.001% to about 0.5%) by weight. It is known that EDTA can be in many forms such as a free acid, disodium, or tetrasodium salts.

In some embodiments, the ophthalmic composition further includes a viscosity-enhancing agent. Examples of suitable viscosity-enhancing agent include polyvinyl alcohol, polyvinyl pyrrolidone, methyl cellulose, hydroxy propyl methylcellulose, hydroxyethyl cellulose, carboxymethyl cellulose, hydroxy propyl cellulose, and any combination thereof. The viscosity-enhancing agent's concentration can range from about 0.01% to about 2% (e.g., from about 0.01% to about 1%, from about 0.01% to about 0.2%, from about 0.01% to about 0.1%, from about 0.1% to about 2%, from about 0.1% to about 1%, or from about 0.1% to about 0.5%) by weight.

In some embodiments, the disorder of the eye is microorganism infection, conjunctivitis, corneal abrasion, ulcerative infectious keratitis, epithelial keratitis, stromal keratitis, or herpesvirus-related keratitis. Examples of the microorganism include bacteria, viruses, fungi, amoebae, and mycobacteria. The infection can be following corneal abrasion or ocular surgery. The composition is useful in the treatment of infections for the conjunctiva and cornea. The broad spectrum of povidone-iodine would allow this ophthalmic composition to be used in cases of ocular conjunctival or corneal infection caused by mycobacteria, viruses, fungi, and amoeba.

In some embodiments, the ophthalmic composition can be in the form of a solution (e.g., an aqueous solution), suspension, emulsion, ointment, cream, gel, or a controlled-release/sustain-release vehicle. For example, the composition may be in the form of a contact lens solution, eyewash, eye drop, and the like.

Through the preparation of povidone iodine and sodium alginate microspheres with different proportion, we observed the microsphere dissolution in the artificial tears. From the dissolution study, we determined the preferred sodium alginate and povidone iodine ratio to be 5:1~1:1.

Through the accelerated stability study, we found that combination of povidone iodine and calcium chloride solutions can effectively stabilize povidone iodine microspheres.

In a preferred embodiment, the ophthalmic composition retains at least 90% of its PVP-I and at least 90% of its steroid after 1 month, 2 months, 3 months, 6 months or 1 year after it is manufactured. This stability is maintained even when the composition is stored at room temperature in a lighted indoor environment of 100 lux to 1000 lux. In one preferred embodiment, the composition is an aqueous solution.

Another aspect of the invention relates to method for treatment or prophylaxis of a disorder of at least one eye tissue, comprising the step of administering an ophthalmic composition of this invention to the eye tissue in need of the treatment or prophylaxis.

The treatment or prophylaxis may be, for example, against infection following surgery, prophylaxis from infection after birth for the newborn, or prophylaxis from accidental contact with contaminating material. Accidental contact with contaminating material may occur, for example, during surgery or during food processing. The composition comprises povidone-iodine in a concentration between 0.01% and 10% by weight.

In the method, the treatment may comprise administering a solution of the invention where the total povidone iodine amount is between 0.001 mg to 5 mg per dose. Further, the dose volume may be between 10 μL to 200 μL or between 50 μL to 80 μL; about one drop per eye. Administration may be between 1 to 24 times a day, between 2 to 4 times a day or between 2 to 24 times a day.

In some embodiments, the disorder of the eye is microorganism infection, conjunctivitis, corneal abrasion, ulcerative infectious keratitis, epithelial keratitis, stromal keratitis, or herpesvirus-related keratitis. Examples of the microorganism include bacteria (e.g., mycobacteria), viruses, fungi, amoebae, and the infection can be following corneal abrasion or ocular surgery.

In some embodiments, the composition is in the form of a solution and the amount of each administration ranges from about 10 μL to 200 μL (e.g., between 50 μL to 80 μL).

In some embodiments, the composition is in the solution form (e.g., aqueous solution) and topically administered to the eye one to twenty-four (e.g., one to four) times a day.

In one embodiment, the method further comprises a step of storing the solution for at least one month, at least two months, at least three months, at least six months, or at least one year before it is administered. The storage may be in a clear bottle (a container that does not substantially block light) in a lighted environment. A lighted environment may be, for example, an indoor lighted environment with about 100 lux to 1000 lux of light.

As used herein, the term "disorder" refers to a condition that shows abnormal symptoms than a patient without the same disorder. It can be microorganism infection, conjunctivitis, corneal abrasion, ulcerative infectious keratitis, epithelial keratitis, stromal keratitis, or herpesvirus-related keratitis.

As used herein, the term "treatment" refers to complete elimination or partially reduction in at least one of the symptoms associated with a disorder.

As used herein, the term "prophylaxis" refers to prevention of at least one of the symptoms associated with a disorder.

As used herein and unless otherwise specified, the term "by weight" in the context of concentration, refers to either weight/weight (ingredient/solution) or weight/volume (ingredient/solvent).

As used herein, the term "about" before a number means that as long as another number is statistically equivalent to or similar as the number following this word, then these two numbers are considered to be about the same and within the cited range. For instance, the number 0.095% may be statistically equivalent to the number 0.1%, thus a general interpreting of the definition of "about 0.1%" would include 0.09% should this interpretation does not cause statistically significant difference.

As used herein, the word "or" has the meaning of both "and" and "or" as the situation or context allows.

DETAILED DESCRIPTION OF THE INVENTION

In a preferred embodiment, the compositions of the present invention are administered topically. The dosage range is 0.001 to 5.0 mg/per eye. Dosage for one eye is understood to be about one drop of solution. One drop of solution may be between 10 μL to 200 μL, between 20 μL and 120 μL, or between about 50 μL to about 80 μL of solution or any values in between. For example, dispensers such as pipettors can dispense fluid drops from at least 1 μL to 300 μL and any value in between.

In a preferred embodiment, the solution may be administered as an eye drop using any of the many types of eye drop dispensers on the market. Although not required, the container for the compositions of the invention may be clear, translucent, and opaque and may contain other properties or combination of properties such as being glass lined, tamper proof, packaged in single or few dose aliquots, and a combination thereof.

Povidone-iodine has the following chemical structure:

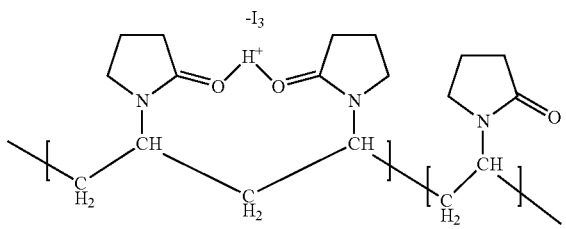

Suitable topical anesthetics for the compositions and methods of the invention include, at least, proparacaine, lidocaine, tetracaine or a derivative or combination thereof.

The compositions of the present invention can be administered as solutions, suspensions, emulsions (dispersions), gels, creams, or ointments in a suitable ophthalmic vehicle. In any of the compositions of this disclosure for topical administration, such as topical administration to the eye, the mixtures are preferably formulated as 0.01 to 2.0 percent by weight solutions in water at a pH of 4.0 to 7.0.

Antimicrobial Preservative

As an optional ingredient, a suitable antimicrobial preservative may be added to prevent multi-dose package contamination. Such agents may include benzalkonium chloride, thimerosal, chlorobutanol, methyl paraben, propyl paraben, phenylethyl alcohol, EDTA, sorbic acid, Onamer M, other agents known to those skilled in the art, or a combination thereof. Typically such preservatives are employed at a level of from 0.001% to 1.0% by weight.

Surfactants

The compositions of the invention may contain one or more optional surfactants (or co-solvents). The solubility of the components of the present compositions may be enhanced by a surfactant or other appropriate co-solvent in the composition. Examples of such co-solvents/surfactants include polysorbate 20, 60, and 80, polyoxyethylene/polyoxypropylene surfactants (e.g. Pluronic F-68, F-84 and P-103), cyclodextrin, tyloxapol, other agents known to those skilled in the art, or a combination thereof. Typically such co-solvents/surfactants are employed at a level of from 0.01% to 2% by weight.

Viscosity-Enhancing Agents

The compositions of the invention may contain an optional viscosity-enhancing agent—that is, an agent that can increase viscosity. Viscosity increased above that of simple aqueous solutions may be desirable to increase ocular absorption of the active compound, to decrease variability in dispensing the formulation, to decrease physical separation of components of a suspension or emulsion of the formulation and/or to otherwise improve the ophthalmic formulation. Examples of such viscosity-enhancing agents include polyvinyl alcohol, polyvinyl pyrrolidone, methyl cellulose, hydroxy propyl methylcellulose, hydroxyethyl cellulose, carboxymethyl cellulose, hydroxy propyl cellulose, other agents known to those skilled in the art, or combinations thereof. Such agents are typically employed at a level of from 0.01% to 2% by weight.

The Formulations

The following two reactions must be considered for the chemistry of PVP-I in aqueous solutions:

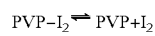     a.

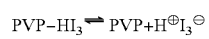     b.

The invention has been described herein by reference to certain preferred embodiments. However, as obvious variations thereon will become apparent to those skilled in the art, the invention is not to be considered as limited thereto. All patents, patent applications, and references cited herein are incorporated by reference in their entireties.

EXAMPLES

Example 1

Preparation of Slow-Releasing Povidone Iodine Ophthalmic Composition

A composition of this invention can be prepared as follows:

Step 1: Povidone iodine and sodium alginate were fully dissolved in water with adjustment of pH to 4.0~5.0 to make Solution A. Microspheres encapsulating povidone iodine were formed when spraying Solution A into a calcium chloride solution. The microspheres were then filtered and dried. The calcium chloride solution concentration was preferred to be 1%~5%.

Step 2: Povidone iodine, a metal ion chelating agent, a pH adjusting agent, microspheres stabilizer, and a suspending agent were poured into proper amount of water and mixed, adjusting pH to 4.0~5.0, to make Solution B, which was filled into the eye drop bottle.

Step 3: Microspheres encapsulating povidone iodine and alginate was poured into Solution B to make a povidone iodine slow-releasing ophthalmic composition.

Example 2

Microspheres Dissolution Study

TABLE 1

(Unit: gram)

| Formulation | sodium alginate/povidone iodine ratio | sodium alginate | povidone iodine | Adding water to |
|---|---|---|---|---|
| 1 | 1:1 | 0.5 | 0.5 | 100 g |
| 2 | 2:1 | 1 | 0.5 | |
| 3 | 3:1 | 1.5 | 0.5 | |
| 4 | 4:1 | 2 | 0.5 | |
| 5 | 5:1 | 2.5 | 0.5 | |
| 6 | 6:1 | 3 | 0.5 | |
| 7 | 7:1 | 3.5 | 0.5 | |

Preparation of 7 formulations of microspheres (listed above in table 1) was conducted according to the method described in Example 1. In Formulation 7, the concentration of sodium alginate was too high to dissolve, which resulted in no microspheres being formed.

Artificial tear configuration: 0.24 g anhydrous calcium chloride and 27.4 g sodium chloride were added into 4000 mL pure water, and the pH of the resultant solution was adjusted using NaOH to 6.8~7.2, for back-up.

Dissolution method: 0.5 g microsphere was added into 100 mL artificial tears and time was recorded. Write down the situation and period of time about the change in color of the microsphere—from brown to white. Table 2 below shows the result of the microsphere dissolution study:

TABLE 2

| Formulation | About 30% corrosion time (hr) | About 80% corrosion time (hr) | Totally corrosion time (hr) |
|---|---|---|---|
| 1 | 0.5 | 4~5 | 8 |
| 2 | 1 | 6~7 | 10 |
| 3 | 2 | 8~10 | 12~16 |
| 4 | 2 | 10~12 | 20~22 |
| 5 | 3 | 15~20 | 24~30 |
| 6 | 4 | >24 | >36 |

Table 2 shows that microspheres of Formulations 1-5 can release for a long time, Formulation 6 was not suitable for slow-release microsphere. So, the ratio of povidone iodine and sodium alginate is preferred to be 1:1~1:5.

Example 3

Stability Studies

Table 3 shows formulations for testing samples and control samples.

TABLE 3

(Unit: gram)

| Formula | PVP-I microspheres | NaCl | CaCl$_2$ | PVP-I powder | glycerol | EDTA-Na | Hydroxylethylcellulose | Add pure water to |
|---|---|---|---|---|---|---|---|---|
| 1 | 1 | 0.9 | 0.08 | 0.1 | 2 | 0.01 | 1.5 | 100 g |
| 2 | 1 | 0.9 | 0.5 | 1 | 2 | 0.01 | 1.5 | |
| 3 | 1 | 0.9 | / | 0.1 | 2 | 0.01 | 1.5 | |
| 4 | 1 | 0.9 | / | 1 | 2 | 0.01 | 1.5 | |
| 5 | 1 | 0.9 | 0.08 | / | 2 | 0.01 | 1.5 | |
| 6 | 1 | 0.9 | 0.5 | / | 2 | 0.01 | 1.5 | |
| 7 | 1 | 0.9 | / | / | 2 | 0.01 | 1.5 | |

Povidone iodine microspheres were made according to method described in Example 1. Stabilities of formulations listed in Table 3 were studied at 40° C. accelerated conditions.

At day 0, 5 and 10, 2 bottles of PVP-I eye drops were taken out and filtered through microfiltration membrane to filter microspheres. A 3% CaCl$_2$ solution was used to rinse the microspheres twice, which were then allowed to dry. The microspheres' corrosion was studied. Table 4 shows accelerated testing results:

TABLE 4

| | 0 day | | 5 days | | 10 days | |
|---|---|---|---|---|---|---|
| Corrosion | Microsphere weight (g) | shape | Microsphere weight (g) | shape | Microsphere weight (g) | shape |
| 1 | 0.311 | Brown and round and smooth | 0.2965 | Brown and round and smooth | 0.2814 | Brown and round and smooth |
| 2 | 0.3225 | Brown and round and smooth | 0.3015 | Brown and round and smooth | 0.3009 | Brown and round and smooth |
| 3 | 0.3014 | Brown and round and smooth | 0 | corrosion | 0 | Corrosion |
| 4 | 0.3005 | Brown and round and smooth | 0 | corrosion | 0 | corrosion |
| 5 | 0.3105 | Brown and round and smooth | 0.2256 | Light Brown and round and smooth | 0.2156 | White round smooth |
| 6 | 0.3114 | Brown and round and smooth | 0.2355 | Light Brown and round and smooth | 0.2096 | White round smooth |
| 7 | 0.3056 | Brown and round and smooth | 0 | corrosion | 0 | corrosion |

Table 4 shows combining CaCl$_2$ and povidone iodine can effectively stabilize the povidone iodine microspheres. Particularly, 0.08%~1.5% CaCl$_2$ with 0.1%~1% povidone iodine can stabilize povidone iodine microspheres.

Example 4

Effect of pH on Corrosion of Microspheres

Miscrospheres made in Example 1 were used for this study. Specifically, 0.5 g microspheres were added to 200 mL solutions of different concentrations of HCl and NaOH, and the pH of the resultant mixture was adjusted to 2.0, 5.0, 7.0, and 9.0, respectively.

The test shows that in the solution of pH 2.0~5.0, the microspheres maintained their round and smooth shape (indicating no or little corrosion); in the solution of pH 7.0~9.0, the microspheres corrosion happed quickly to completion. Therefore, the preferred pH for a microsphere solution is 2.0~5.0. Considering the acid sensitivity of the eye, the preferred pH is 4.0~5.0.

Example 5

Microsphere Formulations

Microspheres were prepared by the following process: First, 1.5 g of sodium alginate was completely dissolved in 80 grams of water, and to the resultant solution was then added 0.5 g povidone-iodine. The mixture was stirred until PVP-I completely dissolved. The pH of the solution was then adjusted to 4~5 and to the solution was filled up to 100 grams by addition of the remaining water. The final solution was allowed to stand by for the next use.

Preparation of 3% solution of calcium chloride: 6 g anhydrous calcium chloride was dissolved in 200 g purified water, stirred sufficiently, for backup.

Filling the sodium alginate/PVP-I solution prepared above in a spray device, and uniformly sprayed to the just-prepared $CaCl_2$ solution. PVP-I microspheres were formed on the surface of $CaCl_2$ solution. The microspheres were allowed to sit in the $CaCl_2$ solution for an hour, making it completely calcified, forming microspheres of a size of about 200 nm~10 μm by membrane filtration. The microspheres was rinsed with a 3% calcium chloride solution and then allowed to dry.

Example 6

Preparation of PVP-I Ophthalmic Solution 1

Hydroxyethylcellulose (0.5 g) was added to 50 g water and was homogenized. To the solution was poured 2 g of glycerol and 0.01 g of EDTA-Na, and the resultant mixture was mixed until homogeneous.

1 g of povidone iodine, 0.1 g of $CaCl_2$, and 0.9 g of NaCl were added into 40 g water, stirred vigorously until completely dissolved. This solution was then poured into the just-made above hydroxyethylcellulose solution and the resultant mixture was homogenized. The pH of the solution was adjusted to 4~5. Povidone iodine microspheres were added to this solution and then water was added to reach the total water weight of 100 g. The final solution was packed separately into 10 g per bottle.

Example 7

Preparation of PVP-I Ophthalmic Solution 2

Microspheres were prepared according to the method in Example 1 with the following materials: 1 g of sodium alginate, 0.5 g of povidone iodine, and 100 g of water (total weight).

An ophthalmic solution was prepared according to Example 6 with the following materials: 5 g of povidone iodine microspheres, 0.9 g of NaCl, 0.2 g of $CaCl_2$, 0.1 g of povidone iodine, 2 g of glycerol, 0.01 g of EDTA-Na, 1.2 g of hydroxyethylcellulose; and total water weight of 100 g.

Example 8

Preparation of PVP-I Ophthalmic Solution 3

Microspheres were prepared according to the method in Example 1 with the following materials: 0.5 g of sodium alginate, 0.5 g of povidone iodine, and 100 g of water (total weight).

An ophthalmic solution was prepared according to Example 6 with the following materials: 15 g of povidone iodine microspheres, 0.9 g of NaCl, 0.4 g of $CaCl_2$, 0.8 g of povidone iodine, 2 g of glycerol, 0.01 g of EDTA-Na, 1.0 g of hydroxyethylcellulose; and total water weight of 100 g.

Example 9

Preparation of PVP-I Ophthalmic Solution 4

Microspheres were prepared according to the method in Example 1 with the following materials: 2.0 g of sodium alginate, 0.5 g of povidone iodine, and 100 g of water (total weight).

An ophthalmic solution was prepared according to Example 6 with the following materials: 20 g of povidone iodine microspheres, 0.9 g of NaCl, 0.5 g of $CaCl_2$, 1.0 g of povidone iodine, 2 g of glycerol, 0.01 g of EDTA-Na, 2.0 g of hydroxyethylcellulose; and total water weight of 100 g.

Example 10

Preparation of PVP-I Ophthalmic Solution 5

Microspheres were prepared according to the method in Example 1 with the following materials: 0.5 g of sodium alginate, 0.5 g of povidone iodine, and 100 g of water (total weight).

An ophthalmic solution was prepared according to Example 6 with the following materials: 25 g of povidone iodine microspheres, 0.9 g of NaCl, 0.5 g of $CaCl_2$, 0.8 g of povidone iodine, 2 g of glycerol, 0.01 g of EDTA-Na, 1.0 g of hydroxyethylcellulose; and total water weight of 100 g.

Example 11

Stability Studies of Compositions of this Invention

The compositions of this invention show unexpected stability compared to the PVP-I solutions in which PVP-I does not exist in microspheres. Specifically, the composition can retain at least 90% of its polyvinylpyrrolidinone-iodine after a period of 1 month even in an environment with light. This indicates that the eye drop solutions (or compositions) of this invention can have long shelf-lives (e.g., at least 3 months, 6 months, 9 months, or a year), even in the light environment, before their application for the treatment or prophyaxis of an eye disorder.

The invention claimed is:

1. An ophthalmic composition for treatment or prophylaxis of a disorder of at least one eye tissue, comprising pharmaceutically acceptable excipients and povidone iodine (PVP-I) wherein PVP-I exists as microspheres formed by PVP-I and sodium alginate and cured by calcium chloride.

2. The ophthalmic composition of claim 1, wherein the concentration of PVP-I is between about 0.1% and about 2.5% by weight.

3. The ophthalmic composition of claim 1, wherein PVP-1 microspheres' size ranges from 200 nm to 10 μm.

4. The ophthalmic composition of claim 1, wherein the weight ratio of PVP-I and sodium alginate in the microspheres is from about 1:1 to about 1:5.

5. The ophthalmic composition of claim 1, further comprising PVP-I solution as a stabilizing agent for the microspheres.

6. The ophthalmic composition of claim 5, wherein the concentration of PVP-I in solution is from about 0.1% to about 5%, weight by weight or weight by volume.

7. The ophthalmic composition of claim 1, wherein the microspheres' concentration is from about 1% to about 25% by weight.

8. The ophthalmic composition of claim 1, further comprising an osmotic pressure regulator, a suspending agent, a chelating agent, a preservative, a coolant, a surfactant, a wetting agent, an antioxidant, or a binder.

9. The ophthalmic composition of claim 8, wherein the osmotic pressure regulator is selected from the group consisting of glycerin, mannitol, and sorbitol; and the osmotic pressure regulator's concentration is from about 0.03% to about 2% by weight.

10. The ophthalmic composition of claim 8, wherein the suspending agent is selected from the group consisting of methylcellulose, hydroxypropyl methyl cellulose, hydroxyethyl cellulose, hydroxyl propyl cellulose, micro crystalline cellulose, sodium carboxymethyl cellulose, and propylene glycol alginate; and the suspending agent's concentration is from about 0.01% to about 2% by weight.

11. The ophthalmic composition of claim 8, wherein the chelating agent is selected from the group consisting of a citric acid salt, ethylenediaminetetraacetic acid (EDTA), and salts of EDTA, and wherein the chelating agent has a concentration ranging from about 0.01% to about 0.05% by weight.

12. The ophthalmic composition of claim 8, wherein the wetting agent is selected from the group consisting of an alcohol, propylene glycol, glycerin, and polyethylene glycol 200-400; and the concentration of the wetting agent is 0.1%~10% by weight.

13. The ophthalmic composition of claim 8, wherein the surfactant is selected from the group consisting of polysorbate 20, polysorbate 60, polysorbate 80, Pluronic F-68, Pluronic F-84, Pluronic P-103, cyclodextrin, tyloxapol, Tween 80, and combinations thereof; and the concentration of the surfactant is from about 0.01% to about 2% by weight.

14. The ophthalmic composition of claim 1, further comprising a topical anesthetic which relieves pain.

15. The ophthalmic composition of claim 14, wherein the topical anesthetic is selected from the group consisting of proparacaine, lidocaine, tetracaine, and combinations thereof.

16. The ophthalmic composition of claim 1, further comprising a penetration enhancer which enhances the penetration of PVP-I into the eye tissue.

17. The ophthalmic composition of claim 16, wherein the penetration enhancer is a topical anesthetic.

18. The ophthalmic composition of claim 1, further comprising an antimicrobial preservative.

19. The ophthalmic composition of claim 18, wherein the antimicrobial preservative is selected from the group consisting of benzalkonium chloride, thimerosal, chlorobutanol, methyl paraben, propyl paraben, phenylethyl alcohol, EDTA, sorbic acid, Onamer M, and combinations thereof.

20. The ophthalmic composition of claim 18, wherein the antimicrobial preservative has a concentration ranging from about 0.001% to about 1.0% by weight.

21. The ophthalmic composition of claim 1, further comprising a viscosity-enhancing agent.

22. The ophthalmic composition of claim 21, wherein the viscosity-enhancing agent is selected from the group consisting of polyvinyl alcohol, polyvinyl pyrrolidone, methyl cellulose, hydroxy propyl methylcellulose, hydroxyethyl cellulose, carboxymethyl cellulose, hydroxy propyl cellulose, and combinations thereof; and the viscosity-enhancing agent's concentration is from about 0.01% to 2% by weight.

23. The ophthalmic composition of claim 1, wherein the disorder of the eye is microorganism infection, conjunctivitis, corneal abrasion, ulcerative infectious keratitis, epithelial keratitis, stromal keratitis, or herpesvirus-related keratitis.

24. The ophthalmic composition of claim 23, wherein the microorganism is bacteria, viruses, fungi, or amoebae.

25. The ophthalmic composition of claim 24, wherein the bacteria is mycobacteria.

26. The ophthalmic composition of claim 1, wherein the composition is used for prophylaxis of infection in the eye following corneal abrasion or ocular surgery.

27. The ophthalmic composition of claim 1, wherein the composition is in the form of a solution, suspension, emulsion, ointment, cream, or gel.

28. A method for treating or prophylaxis of a disorder of at least one eye tissue, comprising the step of administering an ophthalmic composition of claim 1 to the eye tissue in need of the treatment or prophylaxis.

29. The method of claim 28, wherein the disorder is a microorganism infection, conjunctivitis, corneal abrasion, ulcerative infectious keratitis, epithelial keratitis, stromal keratitis, or herpesvirus-related keratitis.

30. The method of claim 29, wherein the disorder is a microorganism infection following corneal abrasion or ocular surgery.

31. The method of claim 30, wherein the microorganism is a bacteria, virus, fungi, or amoebae.

32. The method of claim 31, wherein the bacteria is mycobacteria.

33. The method of claim 28, wherein the composition is in the form of a solution and the amount of each administration is between 10 μL and 200 μL.

34. The method of claim 33, wherein the amount of each administration is between 50 μL and 80 μL.

35. The method of claim 28, wherein the composition is in the solution form and administered to the eye one to twenty-four times a day.

36. The method of claim 28, wherein the composition is in the solution form and administered to the eye one to four times a day.

* * * * *